United States Patent
Dib et al.

(10) Patent No.: US 7,538,106 B2
(45) Date of Patent: May 26, 2009

(54) APPLICATION OF 2-CYANO-10-(2-METHYL-3-(METHYLAMINO)- PROPYL) PHENOTHIAZINE OR A PHARMACEUTICALLY ACCEPTABLE SALT AS MEDICAMENT

(75) Inventors: Michel Dib, Paris (FR); Ahcene Hameg, La Garenne Colombe (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 654 days.

(21) Appl. No.: 10/773,480

(22) Filed: Feb. 6, 2004

(65) Prior Publication Data

US 2004/0171610 A1     Sep. 2, 2004

Related U.S. Application Data

(60) Provisional application No. 60/459,812, filed on Apr. 2, 2003.

(30) Foreign Application Priority Data

Feb. 7, 2003    (FR) .................................. 03 01440

(51) Int. Cl.
*A61K 31/54* (2006.01)
(52) U.S. Cl. .................................. 514/226.2
(58) Field of Classification Search ............... 514/226.2
See application file for complete search history.

(56) References Cited

U.S. PATENT DOCUMENTS 2,877,224 A    3/1959    Jacob et al.

FOREIGN PATENT DOCUMENTS

| WO | WO 01/12265 | 2/2001 |
|---|---|---|
| WO | WO 01/41769 | 6/2001 |

OTHER PUBLICATIONS

Singer et al. [Cinical effects of a sedative neuroleptic: cyamemazine]. Annales Medico-Psychologigues, 1973, vol. 131 (II), No. 4, pp. 540-547, abstract.*

Tilkian et al. Sleep apnea and cardiovascular abnormalities. Primary Cardiology, 1978, vol. 4, No. 9, pp. 84-86, abstract.*

Ahcene Hameg et al., Affinity of Cyamemazine, an anxiolytic antipsychotic drug, for human recombinant dopamine vs. serotonin receptor subtypes, Biochemical Pharmacology (2003, pp. 435-440, vol. 65).

Mickael Naassila et al., Cyamemazine Decreases Ethanol Intake in rats and Convulsions During Ethanol Withdrawal Syndrome in Mice, Psychopharmacology, (1998, pp. 421-428, vol. 140).

* cited by examiner

*Primary Examiner*—Jennifer M Kim
(74) *Attorney, Agent, or Firm*—Balaram Gupta; Craig M. Bell

(57) ABSTRACT

The present invention relates to the application of 2-cyano-10-(2-methyl-3-(methylamino)-propyl)phenothiazine or a pharmaceutically acceptable salt thereof to produce a medicament intended for the treatment of sleep disorders, anxiety disorders, mood disorders, mixed anxiety-depression disorder, acute and chronic psychotic state, addiction to and withdrawal from a substance, extrapyramidal events induced by antipsychotics, or symptomatic dimensions during acute or chronic psychotic states as monotherapy or in combination with other antipsychotics.

4 Claims, No Drawings

APPLICATION OF 2-CYANO-10-(2-METHYL-3-(METHYLAMINO)-PROPYL) PHENOTHIAZINE OR A PHARMACEUTICALLY ACCEPTABLE SALT AS MEDICAMENT

This application claims the benefit of U.S. Provisional Application No. 60/459,812, filed Apr. 2, 2003 and benefit of priority of French Patent Application No. 03/01,440, filed Feb. 7, 2003.

BACKGROUND OF THE INVENTION

1. Field of the Invention

This invention relates to application of 2-cyano-10-(2-methyl-3-(methylamino)propyl)phenothiazine to produce a medicament intended for the treatment of sleep disorders.

2. Description of the Art

More specifically, the present invention relates to the use of 2-cyano-10-(2-methyl-3-(methylamino)propyl)phenothiazine (I) or a pharmaceutically acceptable salt thereof to produce a medicament intended for the treatment of sleep disorders, anxiety disorders (generalized anxiety, panic disorder, with or without agoraphobia, post-traumatic stress condition, anxiety disorder due to a general condition, adaptation disorder with an anxious mood, acute stress condition, nonspecific anxiety disorder, minor anxiety, substance-induced anxiety disorder, and the like), mood disorders (major depressive episode, manic episode, mixed episode, bipolar disorders, nonspecific mood disorder, nonspecific depressive disorder), mixed anxiety-depression disorder, acute and chronic psychotic states (schizophrenia, schizophreniform disorder, schizoaffective disorder, delusional disorder, brief psychotic disorder, substance-induced psychotic disorder, nonspecific psychotic disorder, psychotic disorder due to a general medical condition), behavioral disorders (agitation, aggressiveness, and the like), addiction to and withdrawal from a substance (nicotine, alcohol, benzodiazepine, cocaine, cannabis, hallucinogens, amphetamines), extrapyramidal events induced by antipsychotics (preventive and/or curative treatment), or symptomatic dimensions during acute or chronic psychotic states as monotherapy or in combination with other antipsychotics.

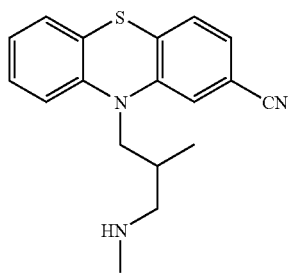

(I)

It is known from the prior art of 1959, GB 805 886, that products derived from 10-phenothiazine can be used as vegetative nervous system inhibitor. The process for producing 2-cyano-10-(2-methyl-3-(methylamino)propyl)phenothiazine (I) is disclosed in GB 805 886.

SUMMARY OF THE INVENTION

More particularly, the present invention relates to the use of 2-cyano-10-(2-methyl-3-(methyl-amino)propyl)phenothiazine (I) or a pharmaceutically acceptable salt thereof to produce a medicament intended for the treatment of sleep disorders.

DETAILED DESCRIPTION OF THE INVENTION

Sleep disorders affect approximately 30 to 35% of the population, according to an enquiry by G. D. Mellinger (Arch. Gen. Psychiatry, 1985, 42, 225-232).

This illness is currently treated mainly with hypnotic benzodiazepines or related benzodiazepines, H1 antihistamines or sedative neuroleptics. There are molecules in development which act on receptors of histamine H3 type or serotoninergic receptors of 5-HT2a type.

It has been found that 2-cyano-10-(2-methyl-3-(methylamino)propyl)phenothiazine (I) exhibits an advantageous binding profile with regard to the receptors with a very good affinity ratio with regard to 5-HT2a/D2 and an excellent selectivity with regard to the muscarinic M1 receptor in comparison with the other muscarinic M2 and M3 receptors. These results make it possible to affirm that 2-cyano-10-(2-methyl-3-(methylamino)propyl)phenothiazine has a very good tolerance profile in particular with fewer extra-pyramidal effects and fewer anticholinergic effects. This is because, according to Can. J. Psychiatry, 2002, 47(1), 27-38, the risk of appearance of extrapyramidal events during antipsychotic treatment is inversely proportional to the degree of binding to the 5-HT2a receptors and to the 5-HT2a/D2 affinity ratio. Furthermore, 2-cyano-10-(2-methyl-3-(methylamino)-propyl)phenothiazine exhibits a high affinity for 5-HT2c receptors, the role of which in anxiety disorders is currently well established.

The results of this study of binding to these various membrane receptors of central neuromediators of human origin are presented in Table 1.

TABLE 1

| Receptors | 2-Cyano-10-(2-methyl-3-(methylamino)-propyl)phenothiazine | |
|---|---|---|
| | $IC_{50}$ (nM) | $K_i$ (nM) |
| D2 (h) | 31 | 12 |
| $M_1$ (h) | 21 | 17 |
| $M_2$ (h) | 368 | 251 |
| $M_3$ (h) | 5490 | 3920 |
| $5\text{-}HT_{1A}$ (h) | 460 | 184 |
| $5\text{-}HT_{2A}$ (h) | 9.0 | 1.5 |
| $5\text{-}HT_{2c}$ (h) | 23 | 8.5 |
| $H_1$ (h) | 22 | 9.3 |

These excellent results make it possible to say that the side effects will be reduced in comparison with the currently existing products.

The sedative activity of the product was determined with mice according to an actimetry test. The actimeter is a device composed of 6 transparent cages in which the animals are individually placed. Photoelectric cells make it possible to detect movements in the cages (by cutting the beam). The spontaneous motor activity is recorded for 10 minutes. The results are expressed in the mean form and in the form of percentage of activity with respect to the control batch. The results are expressed in Table 2.

TABLE 2

| | Doses mg/kg | | | |
|---|---|---|---|---|
| | 0.75 | 1 | 2 | 4 |
| % of activity/control | 61% | 63% | 26% | 9% |

Mention may in particular be made, as pharmaceutically acceptable salts, of the addition salts with inorganic acids, such as hydrochloride, sulfate, nitrate or phosphate, or organic acids, such as acetate, propionate, succinate, oxalate, benzoate, fumarate, maleate, methanesulfonate, isethionate, theophyllineacetate, salicylate, phenolphthalinate, methylenebis(β-hydroxynaphthoate) or derivatives from substitution of these derivatives.

The medicaments are composed of 2-cyano-10-(2-methyl-3-(methylamino)propyl)phenothiazine (I) or a pharmaceutically acceptable salt thereof, in the pure state or in the form of a composition in which it is combined with any other pharmaceutically compatible product, which can be inert or physiologically active. The medicaments according to the invention can be employed orally or parenterally.

The present invention relates to the use of 2-cyano-10-(2-methyl-3-(methylamino)propyl)-phenothiazine (I) or a pharmaceutically acceptable salt thereof for the preparation of pharmaceutical compositions.

Tablets, pills, powders (cachets, gelatin capsules) or granules can be used as solid compositions for oral administration. In these compositions, the active principle according to the invention is mixed with one or more inert diluents, such as starch, cellulose, sucrose, lactose or silica, under a stream of argon. These compositions can also comprise substances other than the diluents, for example one or more lubricating agents, such as magnesium stearate or talc, a coloring agent, a coating (dragées) or a glaze.

Pharmaceutically acceptable solutions, suspensions, emulsions, and syrups and elixirs comprising inert diluents, such as water, ethanol, glycerol, vegetable oils or liquid paraffin, can be used as liquid compositions for oral administration. These compositions can comprise substances other than the diluents, for example wetting, sweetening, thickening, flavoring or stabilizing products.

The sterile compositions for parenteral administration can preferably be suspensions, emulsions or aqueous or nonaqueous solutions. Water, propylene glycol, a polyethylene glycol, vegetable oils, in particular olive oil, injectable organic esters, for example ethyl oleate, or other suitable organic solvents can be employed as solvent or vehicle. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The doses depend on the desired effect, on the duration of the treatment and on the administration route used; they are generally between 10 and 300 mg per day orally for an adult with unit doses ranging from 10 to 300 mg of active substance.

Generally, the doctor will determine the appropriate dosage depending on the age, weight and all the other factors specific to the subject to be treated.

The following examples illustrate medicaments according to the invention:

EXAMPLE A

Tablets comprising a dose of 25 mg of active product are prepared according to the usual technique. These tablets have the following composition:

| Product | 25 mg |
|---|---|
| Lactose | 60 mg |
| Wheat starch | 45 mg |
| Hydrated silica | 4.5 mg |
| Alginic acid | 2.25 mg |
| Talc | 0.75 mg |
| Magnesium stearate | 0.90 mg |

EXAMPLE B

An injectable solution comprising 1 g of active product is prepared. This solution has the following composition:

| Product | 1 g |
|---|---|
| Ascorbic acid | 0.1 g |
| Monothioglycerol | 0.3 g |
| Polyethylene glycol 400 | 0.02 g |
| Water for Injections | q.s. for 100 ml |

The invention also relates to the process for the preparation of medicaments of use in the treatment of sleep disorders which consists in mixing 2-cyano-10-(2-methyl-3-(methylamino)propyl)phenothiazine (I) or its pharmaceutically acceptable salts with one or more compatible and pharmaceutically acceptable diluents and/or adjuvants.

What is claimed is:

1. A method of treating a patient for sleep disorders selected from the group consisting of insomnia and sleep apnea comprising the oral or parenteral administration of a therapeutically effective amount of from about 10 mg to about 300 mg of 2-cyano-10-(2-methyl-3-(methylamino) propyl)phenothiazine (I) or a pharmaceutically acceptable salt thereof.

2. The method as set forth in claim 1 wherein said sleep disorder is primary insomnia.

3. The method as set forth in claim 1 wherein said sleep disorder is insomnia related to another mental disorder.

4. The method as set forth in claim 1 wherein said sleep disorder is obstructive sleep apnea. disease is anxiety disorder.

* * * * *

UNITED STATES PATENT AND TRADEMARK OFFICE
CERTIFICATE OF CORRECTION

| | | |
|---|---|---|
| PATENT NO. | : 7,538,106 B2 | Page 1 of 1 |
| APPLICATION NO. | : 10/773480 | |
| DATED | : May 26, 2009 | |
| INVENTOR(S) | : Michel Dib et al. | |

It is certified that error appears in the above-identified patent and that said Letters Patent is hereby corrected as shown below:

On the Title page, under "Other Publications", in column 2, line 1, delete "[Cinical" and insert
-- [Clinical --, therefor.

On the Title page, under "Other Publications", in column 2, line 2, delete "Psychologigues," and insert
-- Psychologiques, --, therefor.

In the Claims:
In column 4, line 57-58, in Claim 4, after "apnea." delete "disease is anxiety disorder.".

Signed and Sealed this
Nineteenth Day of April, 2011

David J. Kappos
*Director of the United States Patent and Trademark Office*